(12) United States Patent
Shin et al.

(10) Patent No.: US 10,950,337 B1
(45) Date of Patent: Mar. 16, 2021

(54) ASPECT SCORE ESTIMATING SYSTEM AND METHOD

(71) Applicant: Heuron Co., Ltd., Incheon (KR)

(72) Inventors: Dong Hoon Shin, Incheon (KR); Su Min Jung, Gwangju-si (KR)

(73) Assignee: Heuron Co., Ltd., Incheon (KR)

( * ) Notice: Subject to any disclaimer, the term of this patent is extended or adjusted under 35 U.S.C. 154(b) by 0 days.

(21) Appl. No.: 16/652,320

(22) PCT Filed: Sep. 5, 2019

(86) PCT No.: PCT/KR2019/011476
§ 371 (c)(1),
(2) Date: Mar. 30, 2020

(87) PCT Pub. No.: WO2020/111463
PCT Pub. Date: Jun. 4, 2020

(30) Foreign Application Priority Data

Nov. 29, 2018 (KR) .......................... 10-2018-0151378

(51) Int. Cl.
*G06T 7/00* (2017.01)
*G06T 5/00* (2006.01)
(Continued)

(52) U.S. Cl.
CPC ............. *G16H 30/40* (2018.01); *G06T 5/002* (2013.01); *G06T 7/0014* (2013.01); *G16H 50/20* (2018.01);
(Continued)

(58) Field of Classification Search
None
See application file for complete search history.

(56) References Cited

U.S. PATENT DOCUMENTS

| | | | |
|---|---|---|---|
| 2016/0058423 A1* | 3/2016 | Kim | A61B 8/5223 600/407 |
| 2016/0148376 A1* | 5/2016 | Ryu | A61B 8/5223 382/131 |

(Continued)

FOREIGN PATENT DOCUMENTS

KR  10-2012-0041468 A  5/2012
KR  10-2016-0018033 A  2/2016

(Continued)

OTHER PUBLICATIONS

Notice of Preliminary Rejection of KR Patent Application No. 10-2018-0151378 with English Translation.
(Continued)

*Primary Examiner* — Jiangeng Sun
(74) *Attorney, Agent, or Firm* — Sughrue Mion, PLLC

(57) ABSTRACT

Disclosed are an ASPECT score estimating system and a method thereof which estimate an ASPECT score which is a factor for identifying the stroke diseases from the brain CT images and a configuration including a pre-processing step of normalizing and standardizing a feature of an image dataset; a segmenting step of separating each lesion from an CT image which is classified into a supra ganglionic level and a ganglionic level; and a determining step of determining whether the lesion is a stroke by independently building a neural network which learns a positive/negative image for each lesion is provided to estimate an ASPECT score which is an objective indicator for diagnosing a condition of the stroke patient using a brain CT image of the patient.

1 Claim, 10 Drawing Sheets

(51) Int. Cl.
*G16H 30/40* (2018.01)
*G16H 50/20* (2018.01)

(52) U.S. Cl.
CPC ............ *G06T 2207/10081* (2013.01); *G06T 2207/30016* (2013.01); *G06T 2207/30096* (2013.01)

(56) References Cited

U.S. PATENT DOCUMENTS

| | | | | |
|---|---|---|---|---|
| 2016/0171299 | A1* | 6/2016 | Lee | G06F 3/017 382/128 |
| 2019/0026892 | A1* | 1/2019 | Ryu | A61B 8/0825 |
| 2019/0246904 | A1* | 8/2019 | Kim | A61B 5/7267 |

FOREIGN PATENT DOCUMENTS

| | | |
|---|---|---|
| KR | 10-2016-0072676 A | 6/2016 |
| KR | 10-1740464 B1 | 5/2017 |

OTHER PUBLICATIONS

Final Notice of Preliminary Rejection of KR Patent Application No. 10-2018-0151378 with English Translation.
Notice of Allowance in KR Patent Application No. 10-2018-0151378 with English Translation.
Su-min Jung et al., "Estimating Aspect Score for Stroke from Brain CT Images Based-on Deep-Learning", Advanced Science and Technology Letters, vol. 150 (AST 2018), pp. 342-346.
Communication dated Aug. 4, 2020 by the Korean Patent Office in application No. 10-2018-0151378.
"Global Atlas on Cardiovascular Disease Prevention and Control. Geneva", World Health Organization, 2011.
Philip A Barber et al., "Validity and reliability of a quantitative computed tomography score in predicting outcome of hyperacute stroke before thrombolytic therapy", The Lancet, May 13, 2000, pp. 1670-1674, vol. 355.
J. Pfaff et al., "e-Aspects Correlates with and Is Predictive of Outcome after Mechanical Thrombectomy", American Journal of Neuroradiology, Aug. 2017, pp. 1594-1599.

* cited by examiner (a)

(b)

(c)

(d)

(a)  (b)

(a)            (b)

(a)

(b)

ASPECT SCORE ESTIMATING SYSTEM AND METHOD

CROSS REFERENCE TO RELATED APPLICATIONS

This application is a National Stage of International Application No. PCT/KR2019/011476 filed Sep. 5, 2019, claiming priority based on Korean Patent Application No. 10-2018-0151378 filed Nov. 29, 2018.

TECHNICAL FIELD

The present invention relates to an ASPECT score estimating system and method, and more particularly, to an ASPECT score estimating method from a brain CT image to estimate an ASPECT score from a brain CT image of stroke patients based on image processing and a neural network.

BACKGROUND ART

Stroke is a disease which causes brain damages due to blockage or rupture of blood vessels which supply blood to the brain, and thus causes physical disability. The stroke is an important cause of death worldwide and classified as a high risk disease which causes permanent disability even though it does not lead to death.

Conventionally, the stroke has been mainly regarded as a disease of the elderly. However, recently, as the stroke frequently occurs even in the thirties and forties, the stroke is recognized as a very dangerous disease which broadly occurs not only in the elderly, but also in young adults and middle-aged people (see Non-Patent Documents 1 and 2).

There are two types of stroke including "ischemic stroke" which is caused by the blockage of blood vessels which supply blood to the brain and "cerebral hemorrhage" which causes bleeding due to the bursting of blood vessels which are connected to the brain.

The ischemic stroke accounts for about 80% of the total strokes and most of the ischemic stroke is generated due to the blockage of the blood vessel, which supplies oxygen and nutrients to the brain, caused by thrombosis which is a coagulated blood clot.

In order to diagnose the stroke, various tests have been developed and among the various tests, a method which utilizes computed tomography (CT) may allow the test to be quickly performed.

Therefore, the test method based on the CT has an advantage of being able to test quickly, so that it is considered as a test method suitable for a characteristic of the stroke disease for which prompt response is essential.

Further, the cerebral hemorrhage can be observed through the CT immediately after the bleeding occurs. Therefore, in order to treat the ischemic stroke, the CT is useful as a tool which surely identifies cerebral hemorrhage prior to the use of thrombolytic which dissolves the clots to unclog the blood vessels.

Further, the CT is also important for the progress observation of the cerebral hemorrhage after the usage of thrombolytic.

In the meantime, as a representative indicator of the stroke, the Alberta stroke program early CT (ASPECT) score is used.

The ASPECT score divides a middle cerebral artery (MCA) region into 10 predefined anatomical regions and assess the presence of early infarct signs with substantial low risk for NCCT (see Non-Patent Document 3).

The ASPECT score has been proved as a powerful predictor to diagnose a condition of the stroke patients.

However, determination of early signs of ischemia and conversion to the ASPECT score have significant interrater variability, which is influenced by post experience among other factors (See Non-Patent Document 4).

That is, the ASPECT score assesses the disease by calculating a degree of the stroke progression of the user to be 0 to 10 points and this allows medical staffs to use the ASPECT score as a key indicator to determine a treatment method of the user and predict a prognosis of the user.

However, when a medical specialist estimates the ASPECT score, an estimation value may vary depending on the career and experience of the medical specialist due to the user's initial sign and complexity of the image.

Such scoring variability has a negative influence on a decision making process for patient clinical outcomes.

Therefore, it is demanded to develop a technology which objectifies and automates the ASPECT score based on the image processing and deep learning technology to estimate the ASPECT score.

RELATED ART DOCUMENT (Non-Patent Document 1) Global atlas on cardiovascular disease prevention and control. Geneva, World Health Organization, 2011.
(Non-Patent Document 2) WHO Cardiovascular Diseases Fact Sheet No. 317. Updated March 2013, http://www.who.int/mediacentre/factsheets/fs317/en/
(Non-Patent Document 3) Barber P A, Demchuk A M, Zhang J, et al. 'Validity and reliability of a quantitative computed tomography score in predicting outcome of hyperacute stroke before thrombolytic therapy: ASPECTS Study Group-Alberta Stroke Programme Early CT Score.' Lancet 2000; 355:1670-74 CrossRef Medline
(Non-Patent Document 4) PFAFF, J., et al. 'e-ASPECTS Correlates with and Is Predictive of Outcome after Mechanical Thrombectomy.' American Journal of Neuroradiology, 2017.

DISCLOSURE

Technical Problem

An object of the present invention is to solve the problems as described above and provide an ASPECT score estimating system and a method therefor which estimate the ASPECT score which is a factor for identifying the stroke diseases from the brain CT images.

Another object of the present invention is to provide an ASPECT score estimating system and a method therefor which reduce scoring variability when the ASPECT score is estimated based on the image processing and the deep learning technology.

Still another object of the present invention is to provide an ASPECT score estimating system and a method therefor which may improve the reliability of the estimated ASPECT score.

Technical Solution

In order to achieve the objects as described above, the ASPECT score estimating method according to the present invention includes a pre-processing step of normalizing and standardizing a feature of an image dataset; a segmenting step of separating each lesion from an CT image which is classified into a supra ganglionic level and a ganglionic level; and a determining step of determining whether the lesion is a stroke by independently building a neural network which learns a positive/negative image for each lesion.

Further, in order to achieve the objects as described above, the ASPECT score estimating system according to the present invention includes a pre-processing unit which normalizes and standardizes a feature of an image dataset; an image processing unit which separates each lesion from an CT image which is classified into a supra ganglionic level and a ganglionic level; and a determining unit which determines whether the lesion is a stroke by independently building a neural network which learns a positive/negative image for each lesion.

Advantageous Effects

As described above, according to an ASPECT score estimating system and a method therefor according to the present invention, it is possible to estimate an ASPECT score which is an objective indicator to diagnose a condition of a stroke patient using brain CT images of a patient.

Further, according to the present invention, due to the nature of the stroke diseases which requires a prompt prescription, the ASPECT score can be used as a reliable indicator which prevents the problems due to the scoring variability between medical specialists and facilitates the decision of the treatment of the patients in the medical field.

Further, according to the present invention, it is possible to overcome the inaccuracy of the score values according to the carriers of the medical specialists due to the complexity and the expertise of the stroke ASPECT score estimating method by the analysis of the brain CT images.

Further, according to the present invention, it is possible to drastically reduce the manpower, time, and economic costs required for the analysis by automating the entire process of the CT image-based stroke analysis.

BEST MODE

Hereinafter, an ASPECT score estimating system and a method therefor according to an exemplary embodiment of the present disclosure will be described in detail with reference to the accompanying drawings.

Hereinafter, as a dataset used for an algorithm which implements an ASPECT score estimating method according to the present invention, brain CT images of 287 stroke patients whose ASPECT scores are calculated in accordance with judgments of the medical specialist. As the brain CT images for every patient, a total of two sheets of images including one sheet of the ganglionic level and one sheet of the supra ganglionic level are used.

In order to calculate the ASPECT score, it is determined whether it is positive or negative for seven regions of the ganglionic level and three regions of the supra ganglionic level.

The accuracy of the algorithm is determined depending on whether a positive/negative ground truth value for each of 10 lesions of a patient created by the medical specialist matches a positive/negative value for every lesion calculated by the algorithm.

Figure 1:
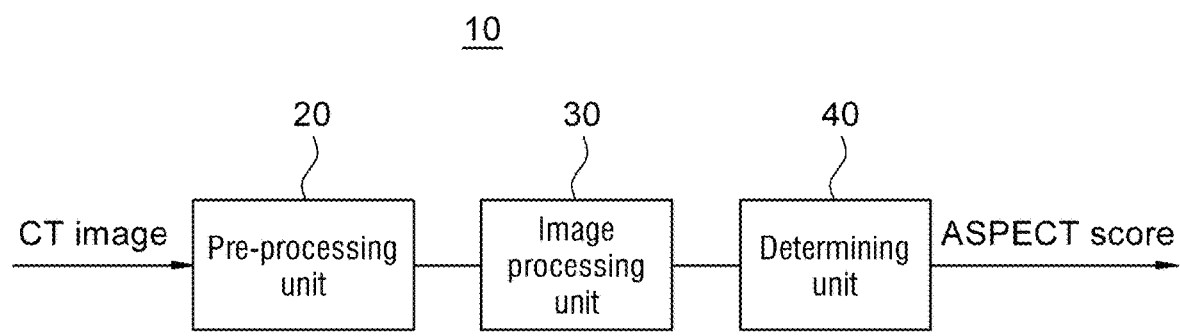
FIG. 1 is a diagram of an ASPECT score estimating system according to an exemplary embodiment of the present invention.

FIG. 1 is a diagram of an ASPECT score estimating system according to an exemplary embodiment of the present invention.

As illustrated in FIG. 1, an ASPECT score estimating system 10 according to an exemplary embodiment of the present invention includes a pre-processing unit 20 which normalizes and standardizes a feature of an image dataset to calculate an ASPECT score based on a brain CT image of a stroke patient, a segmentation image processing unit 30 which separates each lesion in the CT image classified into a supra ganglionic level and a ganglionic level, and a determining unit 40 which independently builds a neural network which learns a positive/negative image for every lesion based on deep learning to determine whether the lesion is the stroke.

The pre-processing unit 20 is communicatively connected to a database which stores and controls CT equipment or CT images captured by the CT equipment to acquire and pre-process the CT images of a patient to estimate an ASPECT score.

Further, an ASPECT score estimating method according to an exemplary embodiment of the present invention includes a pre-processing step of normalizing and standardizing a feature of an image dataset to calculate an ASPECT score based on a CT image of a stroke patient, a segmenting step of separating each lesion from the CT image classified into a supra ganglionic level and a ganglionic level, and a determining step of independently building a neural network which learns a positive/negative image for every lesion based on deep learning to determine whether the lesion is the stroke.

The ASPECT score of the patient is calculated by adding whether lesions are stroke.

Figure 2:
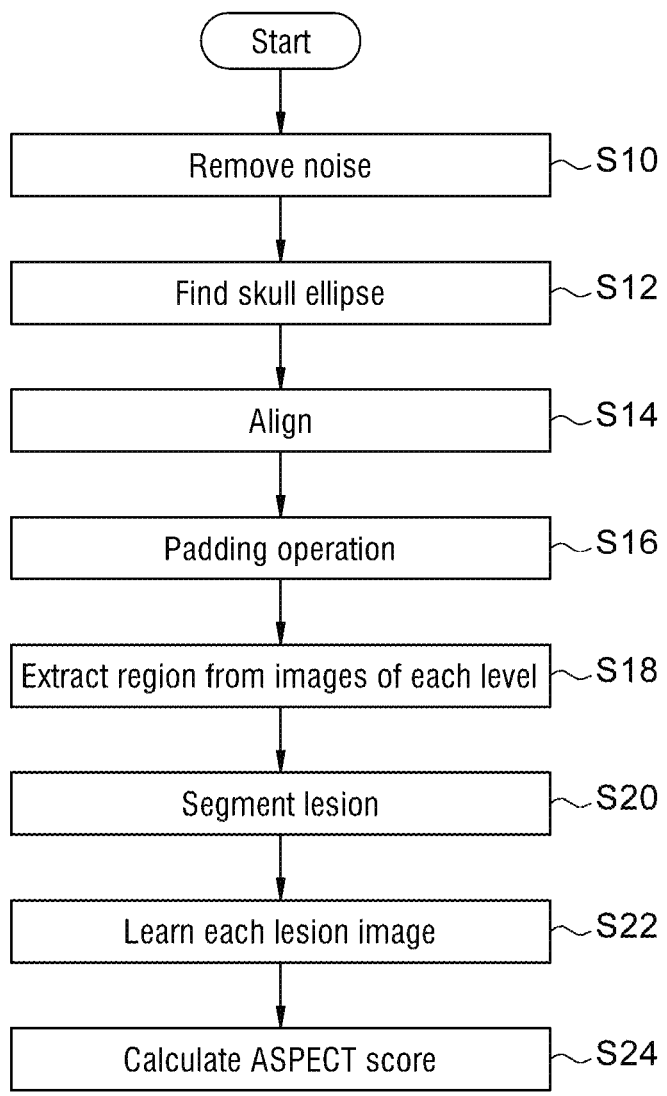
FIG. 2 is a flowchart for explaining an ASPECT score estimating method according to an exemplary embodiment of the present invention step by step.

FIG. 2 is a flowchart for explaining an ASPECT score estimating method according to an exemplary embodiment of the present invention step by step.

In the present exemplary embodiment, along with step-by-step description of the entire algorithm, a test software result of a deep learning-based lesion diagnosing step is examined and the entire algorithm is verified.

(1) Pre-Processing Step

In the pre-processing step, the pre-processing unit 20 performs a function for ensuring a more accurate result in the segmenting step and the deep learning step thereafter by normalizing and standardizing the dataset.

To this end, in the pre-processing step, the pre-processing unit 20 may perform a step of detecting a position of a skull in the brain CT image based on the image processing, an alignment step of aligning the image with respect to a rotation degree and a center point, and a horizontal inverting step in accordance with a lesion-side.

The pre-processed image is standardized as an image centered such that a left brain is a lesion and a center vertical line of the image is a symmetry line of the brain.

In the pre-processing step, the image is optimized to specify a key feature allowing identification of the stroke in the deep-learning based determining step thereafter.

In FIG. 2, the pre-processing step includes a noise removing step S10 of removing a noise in the image, a finding step S12 of finding a skull ellipse to find out a skull from the brain CT image of the patient, and an alignment step S14 of uniformly aligning a position and a rotation degree of the dataset by aligning a position of the image with respect to a center point of the found skull and rotating the image.

Figure 3:
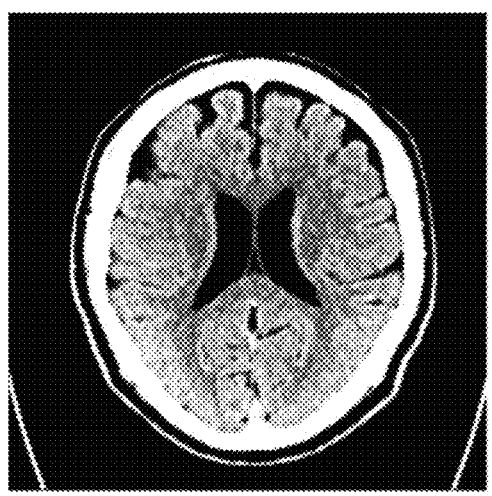
FIG. 3 is an exemplary diagram for explaining a pre-processing step.
Figure 3:
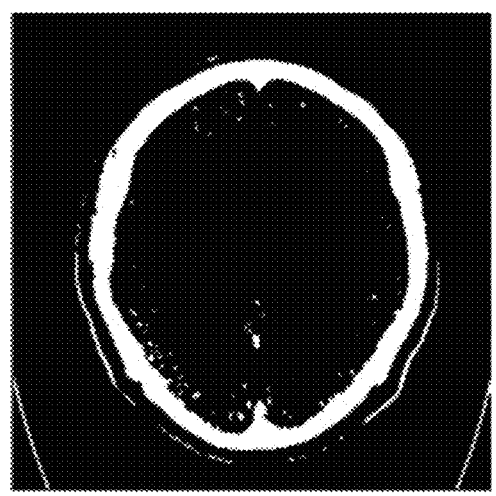
Figure 3:
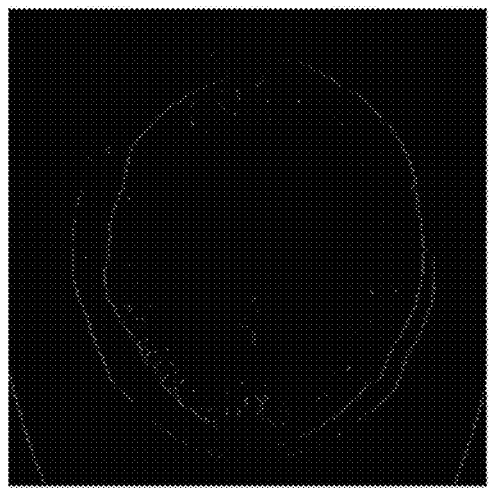
Figure 3:
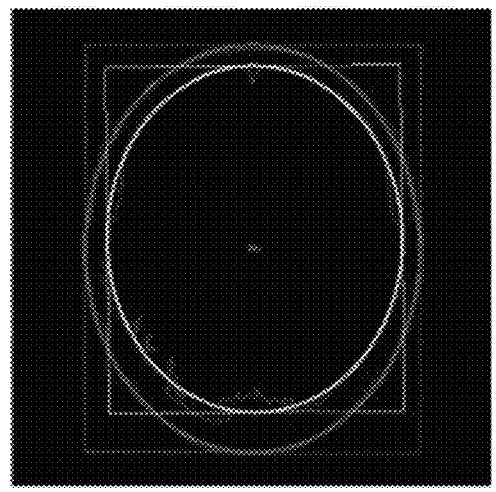

FIG. 3 is an exemplary diagram for explaining a pre-processing step.

FIG. 3A illustrates an image which is convoluted with a Gaussian blur, FIG. 3B illustrates a thresholding image, FIG. 3C illustrates a contour finding image, and FIG. 3D illustrates internal and external ellipses of the skull.

A noise included in the CT image degrades an accuracy of each step included in the pre-processing step for acquiring key features of the brain so that the noise needs to be removed.

Therefore, during the noise removing step S10, as illustrated in FIG. 2A, the entire images are convoluted with the Gaussian blur to remove the noise included in the image.

In the finding step S12, auto thresholding, contour finding, and skull ellipse finding functions are performed.

That is, in the finding step S12, the functions may be separated to find out the internal ellipse and the external ellipse of the skull from the image from which the noise is removed.

As illustrated in FIG. 3B, the auto thresholding function searches an adaptive threshold value in consideration of a distribution of pixel values of the segmented image and induces to remain only pixel information corresponding to the skull.

As illustrated in FIG. 3C, the contour finding function detects an edge based on an image on which the thresholding is completed and as illustrated in FIG. 3D, the skull ellipse finding function finds skull ellipses from the image only having edge information to acquire internal and external ellipse information of the skull.

The alignment step S14 is a pre-processing step for maintaining a consistency of the dataset and the consistency of the dataset is necessary to increase learning and classifying accuracy in deep learning-based learning and determining which identify the stroke thereafter.

Figure 4:
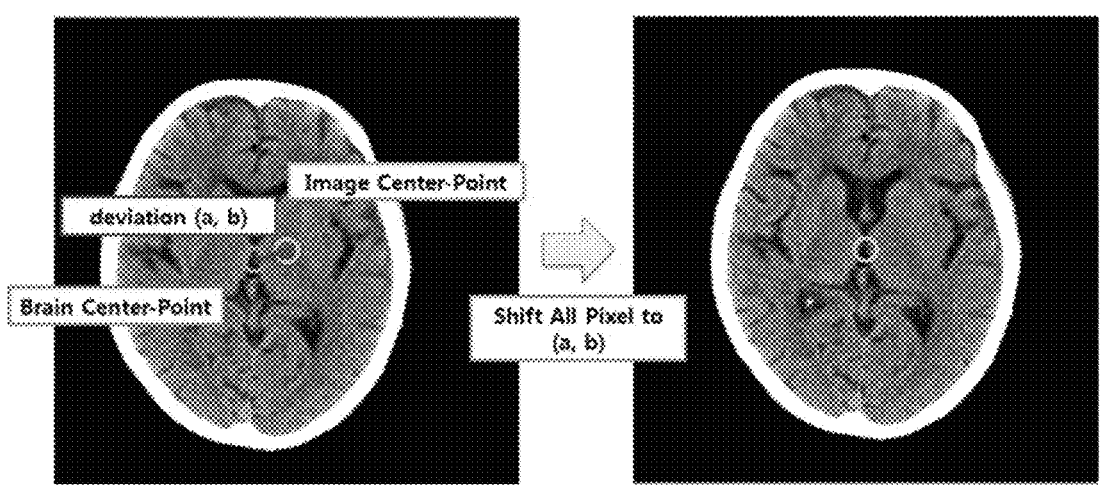
FIG. 4 is a view for explaining a center-point alignment process.
Figure 5:
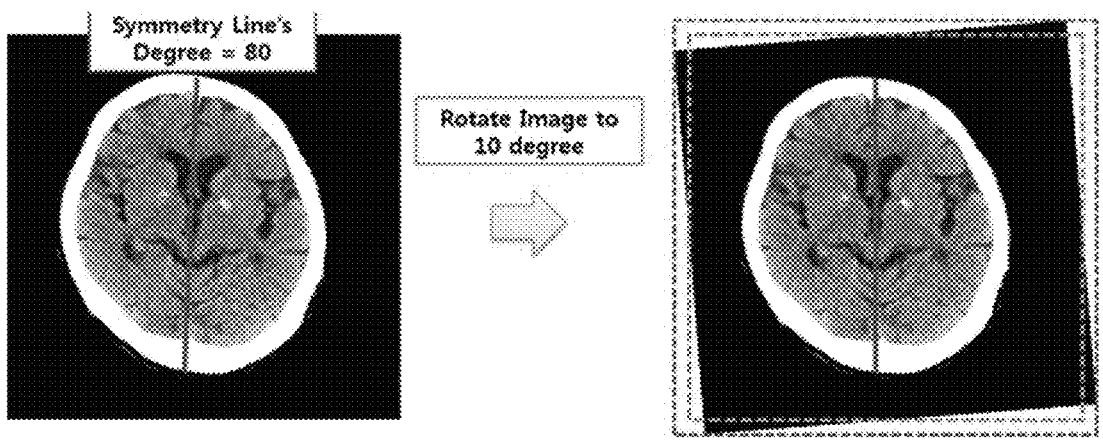
FIG. 5 is a view for explaining a rotation alignment.

FIG. 4 is a view for explaining a center point alignment process and FIG. 5 is a view for explaining a rotation alignment.

That is, when the medical specialist photographs the brain CT image of the stroke patient, there is a difference in the position of the skull of the patient so that during the alignment step, center-point alignment and rotation alignment of the skull illustrated in FIGS. 4 and 5 are performed.

Therefore, according to the present invention, the consistency of the position and the rotation of the dataset may be achieved.

Here, the position and rotation alignment of the dataset may be calculated based on skull ellipse information acquired during the pre-processing step.

In the meantime, the pre-processing step may further include a padding step S16 of removing a skull region which is an unnecessary feature to identify the stroke, thereby increasing the learning and classifying accuracy of the subsequent deep learning-based learning and determining step.

Figure 6:
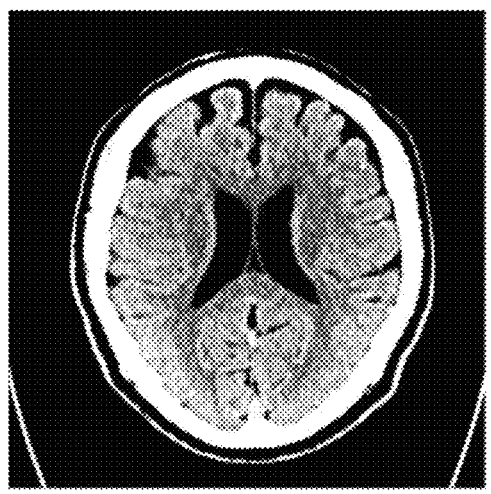
FIG. 6 is a view illustrating images before and after a padding process.
Figure 6:

FIG. 6 is a view illustrating images before and after a padding process.

FIGS. 6A and 6B illustrate an image before the padding process and an image after the padding process, respectively.

That is, during the padding step, as illustrated in FIG. 6A, a region with a predetermined width from the skull ellipses is set as a region of interest (ROI) based on the skull ellipse information acquired during the pre-processing step and a threshold value corresponding to the skull in the CT image is adaptively calculated, and a padding operation is performed based on the calculated threshold value.

(2) Segmenting Step

The segmenting step is a step for separating a total of 10 regions to estimate an ASPECT score from the brain CT image in which seven regions are extracted from the ganglionic level and three regions are extracted from the supra ganglionic level (S18).

Figure 7:
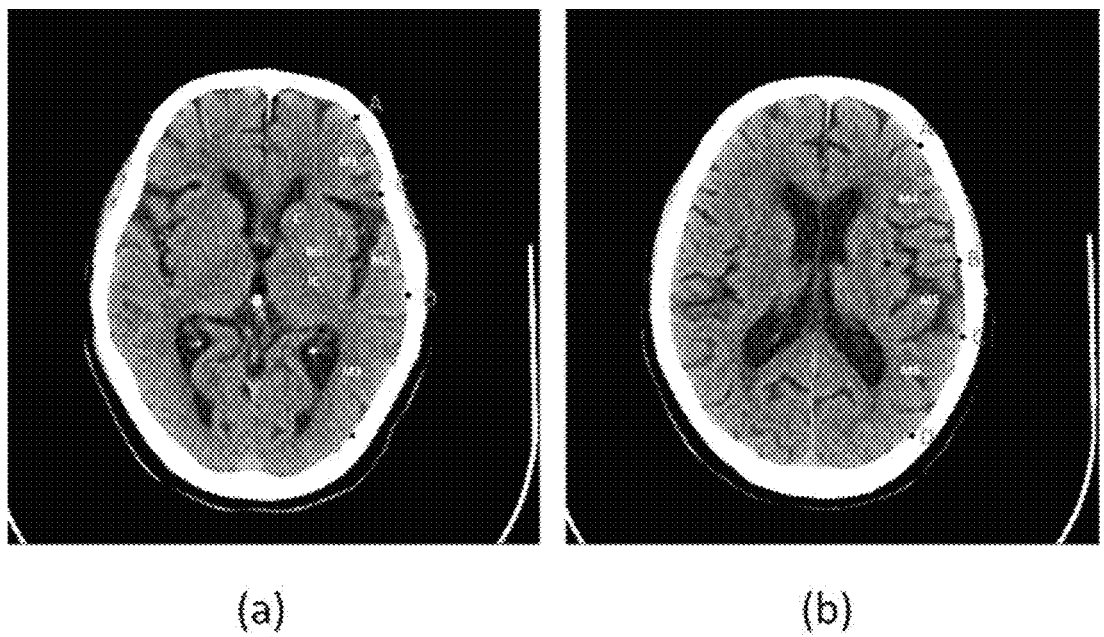
FIG. 7 is an exemplary diagram for explaining segmentation of a ganglionic level and segmentation of a supra ganglionic level.

FIG. 7 is an exemplary diagram for explaining segmentation of a ganglionic level and segmentation of a supra ganglionic level.

Images of the ganglionic level and the supra ganglionic level have feature points which are necessarily generated when the stroke occurs and the legions are segmented using the skull ellipse information acquired in the pre-processing step and the feature points based on an image processing technique.

FIG. 7 illustrates a reference using the feature point and in FIGS. 7A and 7B, feature points used for the ganglionic level and the supra ganglionic level are illustrated with red points.

The image processing unit 30 of the ASPECT score estimating system 10 according to the present invention searches the feature point based on a predetermined segmentation criterion and then geometrically connects the feature points to segment the lesion.

Figure 8:
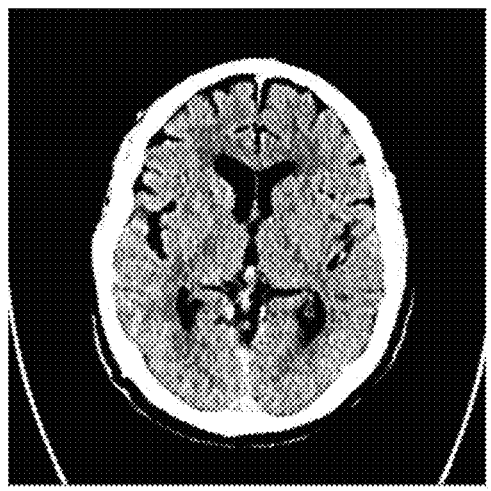
FIG. 8 is a view illustrating a segmentation result of a ganglionic level.
Figure 8:
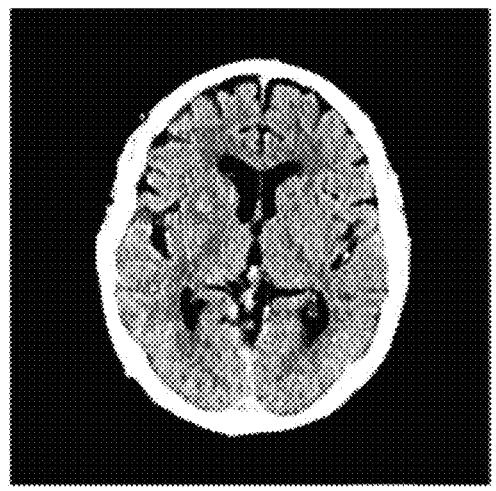

FIG. 8 is a view illustrating a segmentation result of a ganglionic level.

FIGS. 8A and 8B illustrate an image before segmentation and an image after segmentation, respectively.

In FIG. 8, it is confirmed that seven legions extracted from the ganglionic level are segmented.

Each lesion has a form which is not clearly identified by the pixel value so that the lesion is optimized to approximate a segmentation criteria established by the opinion of the medical specialist.

(3) Diagnosis of Legion Based on Deep Learning

In step S22, the determining unit 40 crops lesion images from the entire image in accordance with the segmentation result and performs supervised learning on the cropped image including positive/negative information with a neural network configured for every lesion.

Each neural network learns based on convolutional neural network (CNN), is configured by six hidden layers and two dropout layers for preventing overfitting, and uses a rectified linear unit (ReLU) as an activation function.

Therefore, the determining unit 40 performs learning and classifying on each lesion in an independent neural network. The number of neural networks which determines the lesion to be positive means the number of lesions with a stroke disease. Therefore, the determining unit 40 calculates a final ASPECT score based on a corresponding value in accordance with the following Equation 1 (S24).

$$AspectScore = 10 - \sum_{k=1}^{10} \text{if } (L_k == \text{positive}) \quad \text{[Equation 1]}$$

(4) Verification

In the embodiment, the ASPECT score estimated through the processes as described above is verified as a test result of M4 lesion of the supra ganglionic level by developing a prototype for predicting an accuracy of the neural network for each lesion.

Figure 9:
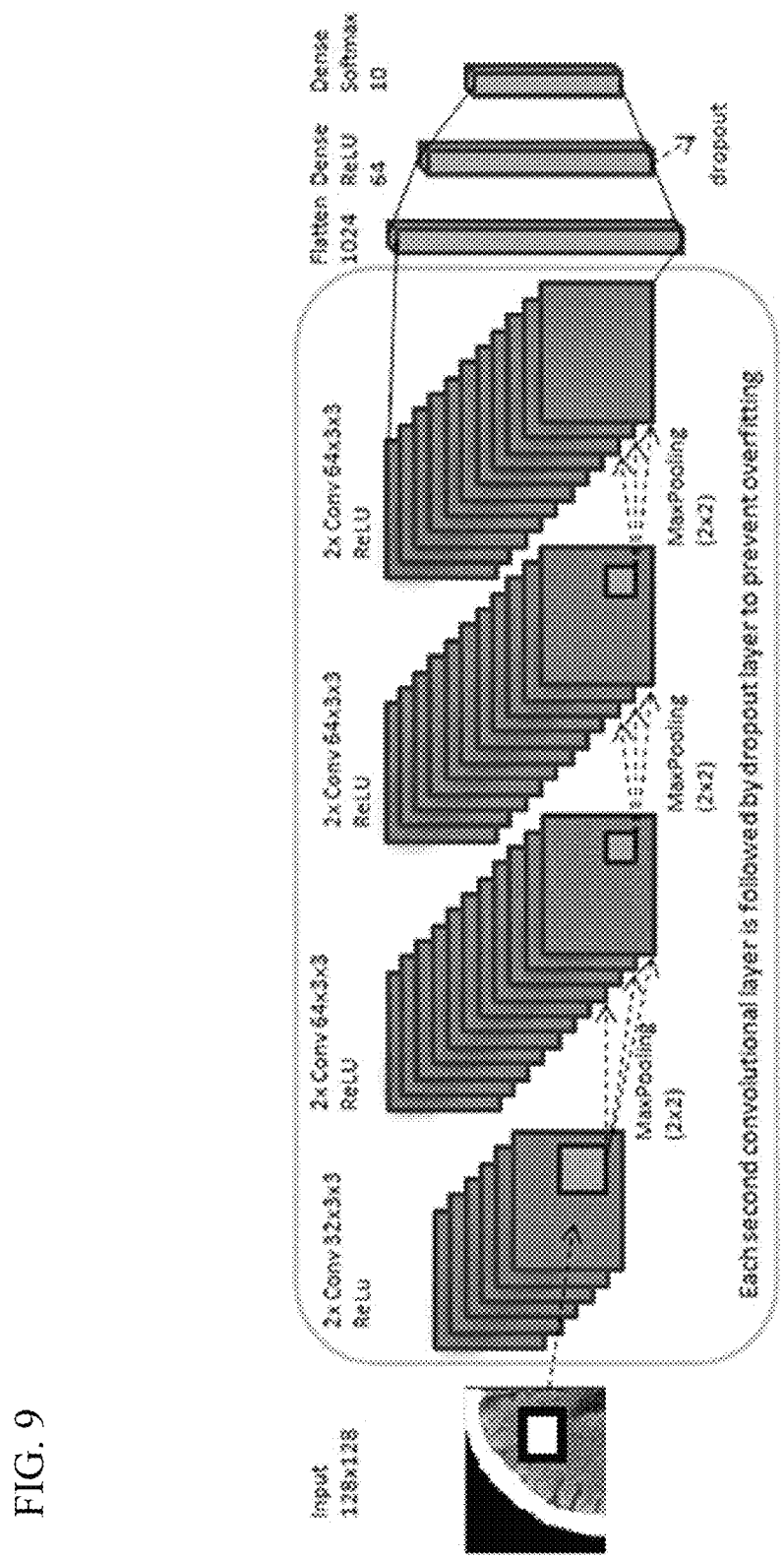
FIG. 9 is a view illustrating a neural network structure of each lesion.

FIG. 9 is a view illustrating a neural network structure of each lesion.

As illustrated in FIG. 9, during the verifying process, a dataset for 187 patients for the M4 lesion is used and 80% of images is used as a learning dataset and 20% of the image is used as a test dataset.

The accuracy of the prototype test for the M4 region is approximately 70.9%, which is mainly caused due to lack of the dataset and lack of segmentation accuracy.

Based on the prototype verification result, it is understood that the segmentation accuracy of the lesion has a significant influence on the ASPECT score estimation accuracy.

Therefore, an additional test is performed by changing the system so as not to consider the influence by the segmentation.

Input data and a neural network structure are changed so as to estimate the ASPECT score for the entire image without dividing the lesions for the ganglionic level and the supra ganglionic level from the brain CT image.

That is, the ASPECT score estimating system has an independent neural network for the ganglionic level and the supra ganglionic level and receives pre-processed and not-segmented brain CT images of the corresponding level to learn the ASPECT score.

The learning dataset used CT images of 278 stroke patients and ResNet101 was used for the neural network learning.

Bland-Altman plot was used as a performance evaluation algorithm and how close the ASPECT score was to the medical specialist was evaluated using an error between a ground truth for the dataset calculated by the medical specialist and a result value acquired from the neural network.

$$E_p = (G_p - R_p)_{supra} + (G_p R_p)_{ganglionic} \quad \text{[Equation 2]}$$

That is, in accordance with Equation 2, an error between the ground truth value $G_p$ and the result value $R_p$ was independently calculated for a supra ganglionic level and a ganglionic level of a patient p and a value obtained by adding the errors of individual levels was determined as a final error value $E_p$.

Figure 10:
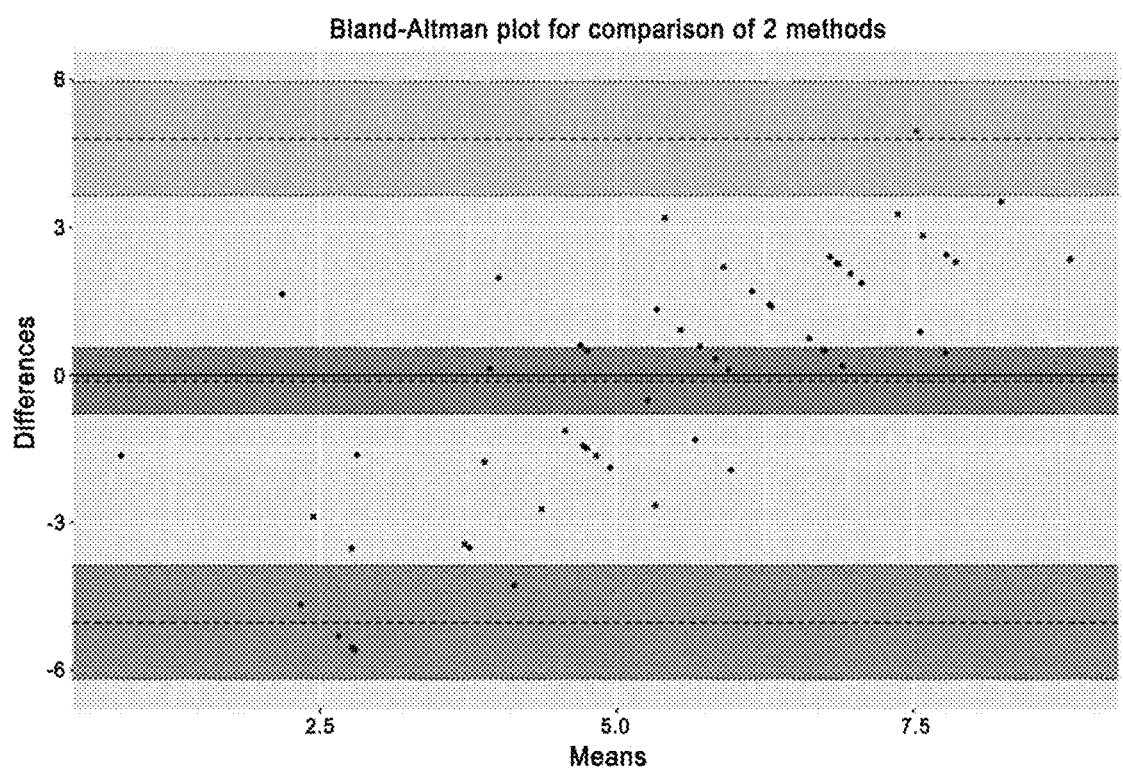
FIG. 10 is a performance evaluation graph.

Table 1 is a table of performance evaluation results and FIG. 10 is a performance evaluation graph acquired by Bland-Altman plot.

TABLE 1

| Mean | Standard deviation | 95% Confidence interval |
|---|---|---|
| 0.1116 | 2.5080 | −0.5453~0.7684 |

In Table 1 and FIG. 10, an error mean was close to "0", but a standard deviation was "2.5080", which showed a high scatter diagram. Therefore, 0.95% confidence interval (CI) of "−0.5453 to 0.7684" was shown.

As described above, according to the present invention, it is possible to estimate the ASPECT score which is an objective indicator for diagnosing a condition of a stroke patient only using CT images.

Further, according to the present invention, due to the nature of the stroke diseases which requires prompt prescription, an ASPECT scoring automation estimation program prevents the problems caused due to the scoring variability between medical specialists and may use the ASPECT score as a reliable indicator which facilitates the decision of the treatment of the patients in the medical field.

According to the verification result, the system described in the present embodiment showed a lower accuracy due to lack of volume of the dataset of the stroke CT images, a reliability issue of the ground truth, and ambiguity of features in the image.

However, since a neural network has a characteristic in that a result is significantly influenced by a quality of the dataset, when the neural network is modified to receive only features specific to the stroke determination by applying a highly reliable measurement result by increase of the dataset and scoring of a plurality of medical specialists and emphasizing and selecting the feature to which the opinion of the medical specialist is reflected during the image pre-processing step, a result with a high accuracy may be obtained.

As described above, even though the invention made by the inventor has been described in detail with exemplary embodiments, it is apparent that the present invention is not limited to the exemplary embodiment but various modifications and changes may be made without departing from the spirit of the present invention.

INDUSTRIAL APPLICABILITY

The present invention is applied to a technology which estimates an ASPECT score which is an objective indicator for diagnosing a condition of a stroke patient using a brain CT image of the patient.

The invention claimed is:

1. An Alberta stroke program early computed tomography (ASPECT) score estimating method based on a brain computed tomography (CT) image of a stroke patient, the method comprising:
    a pre-processing step of normalizing and standardizing a feature of an image dataset, by a pre-processing unit;
    a segmenting step of separating each lesion from a CT image which is classified into a supra ganglionic level and a ganglionic level, by an image processing unit; and
    a determining step of determining whether the lesion is a stroke by independently building a neural network which learns a positive/negative image for each lesion, by a determining unit,
    wherein the pre-processing step includes:
    a noise removing step of removing a noise included in the image by convoluting the entire brain CT image of the patient with a Gaussian blur;
    a finding step of finding a skull to find out a skull from brain CT image;
    an alignment step of constantly aligning a position and a rotation degree of the dataset by aligning a position of the image and rotating the image with respect to a center point of the found skull; and
    a horizontal inverting step in accordance with a lesion-side,
    the finding step includes;

an auto thresholding step of searching a adaptive threshold value in consideration of distribution of pixel values of the segmented image and inducing to remain only pixel information corresponding to the skull;

a contour finding step of detecting an edge based on an image on which the thresholding is completed; and a skull ellipse information acquiring internal and external ellipse information of the skull by searching skull ellipses from the image only having edge information, the CT image is subjected to the pre-processing step to be normalized and standardized as an image centered such that a left brain is a lesion and a center vertical line of the image is a symmetry line of the brain, the determining step includes:

a step of cropping each lesion image from the entire image in accordance with the segmentation result of the segmenting step;

a step of performing supervised learning on the cropped image with a neural network configured for every lesion including positive/negative information; and a step of learning and classifying in a neural network independent for every lesion and calculating a final ASPECT score based on the number of neural networks which determine the lesion to be positive, the determining unit builds an independent neural network for the supra ganglionic level and the ganglionic level, and the neural networks are independently built learn based on a convolutional neural network (CNN), are configured by six hidden layers and two dropout layers for preventing overfitting and a use a rectified linear unit (ReLU) as an activation function.

* * * * *